(12) United States Patent
Nickerson et al.

(10) Patent No.: US 8,681,336 B2
(45) Date of Patent: Mar. 25, 2014

(54) SYSTEM AND METHOD FOR DETERMINING FLUX OF ISOTOPOLOGUES

(75) Inventors: Nicholas R. Nickerson, Kentville (CA);
Jocelyn Elizabeth Egan, Ottawa (CA);
David Andrew Risk, Heatherton (CA)

(73) Assignee: St. Francis Xavier University, Antigonish (CA)

( * ) Notice: Subject to any disclaimer, the term of this patent is extended or adjusted under 35 U.S.C. 154(b) by 65 days.

(21) Appl. No.: 13/417,625

(22) Filed: Mar. 12, 2012

(65) Prior Publication Data

US 2013/0235378 A1    Sep. 12, 2013

(51) Int. Cl.
*G01N 21/59* (2006.01)
*G01J 3/42* (2006.01)

(52) U.S. Cl.
USPC ............................ 356/437; 356/402; 356/432

(58) Field of Classification Search
USPC ........................ 356/432–437, 402; 702/2, 24; 73/864.83, 1.06; 137/3, 897
See application file for complete search history.

(56) References Cited

U.S. PATENT DOCUMENTS

| | | | | |
|---|---|---|---|---|
| 7,369,242 B2 * | 5/2008 | Cole et al. | ............. | 356/436 |
| 7,704,746 B1 * | 4/2010 | White et al. | ............. | 436/56 |
| 2002/0000226 A1 * | 1/2002 | Butnor et al. | ............. | 128/200.24 |
| 2003/0042151 A1 * | 3/2003 | Ando et al. | ............. | 205/781 |
| 2006/0231422 A1 * | 10/2006 | Rhodes et al. | ............. | 205/781 |
| 2009/0301234 A1 * | 12/2009 | Risk | ............. | 73/864.83 |
| 2009/0321279 A1 * | 12/2009 | Holmen et al. | ............. | 205/781 |
| 2010/0055802 A1 * | 3/2010 | Zare et al. | ............. | 436/158 |
| 2010/0198736 A1 * | 8/2010 | Marino | ............. | 705/308 |
| 2010/0241363 A1 | 9/2010 | Keeling et al. | | |
| 2010/0313963 A1 * | 12/2010 | Skinn | ............. | 137/3 |
| 2011/0046896 A1 | 2/2011 | Smajlovic | | |
| 2011/0112772 A1 | 5/2011 | Yost et al. | | |
| 2011/0125413 A1 | 5/2011 | Podlesak et al. | | |
| 2011/0136097 A1 * | 6/2011 | Smajlovic | ............. | 435/4 |
| 2011/0178722 A1 | 7/2011 | Roca et al. | | |
| 2011/0301866 A1 | 12/2011 | Holba et al. | | |
| 2012/0035850 A1 | 2/2012 | Risk et al. | | |
| 2012/0219361 A1 * | 8/2012 | Kim et al. | ............. | 405/129.5 |
| 2012/0300209 A1 * | 11/2012 | Witinski et al. | ............. | 356/409 |

OTHER PUBLICATIONS

Risk, D. et al., Forced diffusion soil flux: A new technique for continuous monitoring of soil gas efflux, Agricultural and Forest Meteorology, 2011.
Nickerson, N. et al., A numerical evaluation of chamber methodologies used in measuring the σ13C of soil respiration, Rapid Communications in Mass Spectrometry, 2009, 23, pp. 2802-2810.

* cited by examiner

*Primary Examiner* — Sang Nguyen
(74) *Attorney, Agent, or Firm* — Bereskin & Parr LLP

(57) ABSTRACT

A method and system comprising measuring concentrations of first and second isotopologues of a gas of interest within a first cavity that is sealably in contact with a soil location through an inlet membrane, and the first cavity being defined by chamber walls having openings covered by outlet membranes. Reference concentrations of the first and second isotopologues are measured in a second cavity having a closed bottom, the second cavity being defined by chamber walls having openings covered by more outlet membranes. Relative flux of the isotopologues can be calculated using the measured concentrations.

32 Claims, 8 Drawing Sheets

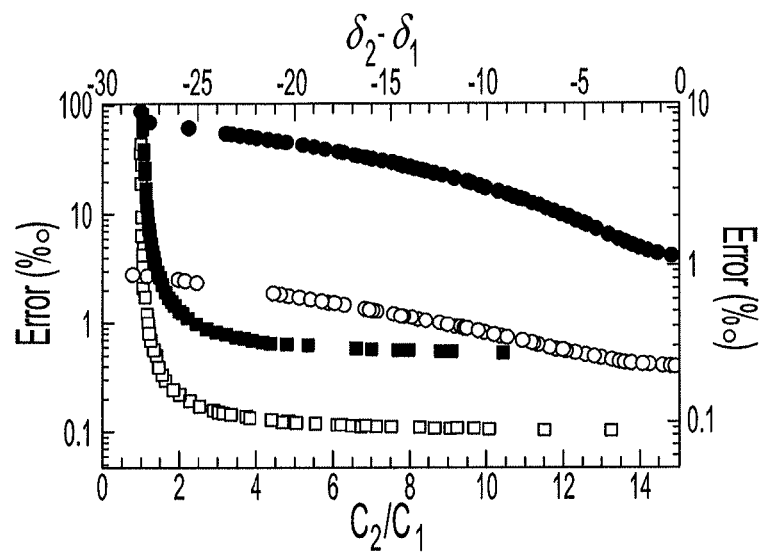
Fig-7
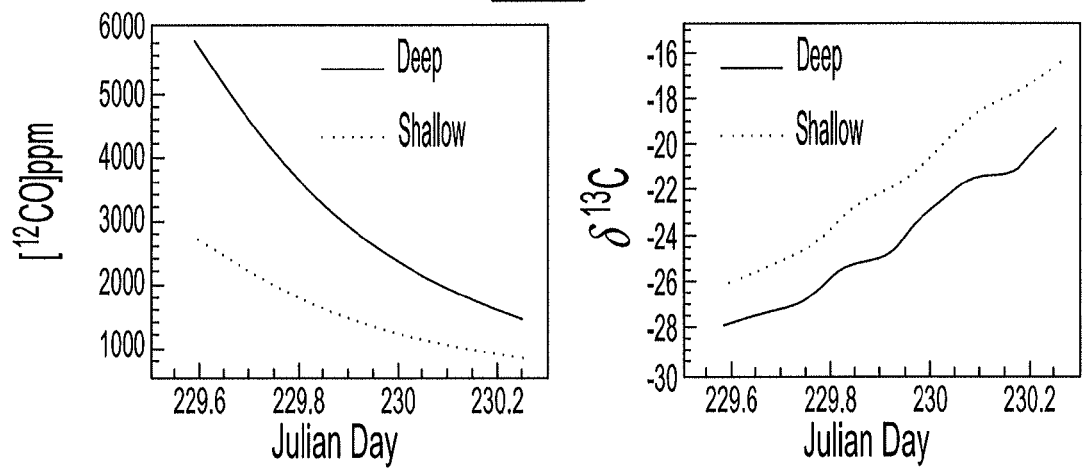
Fig-8A
Fig-8B
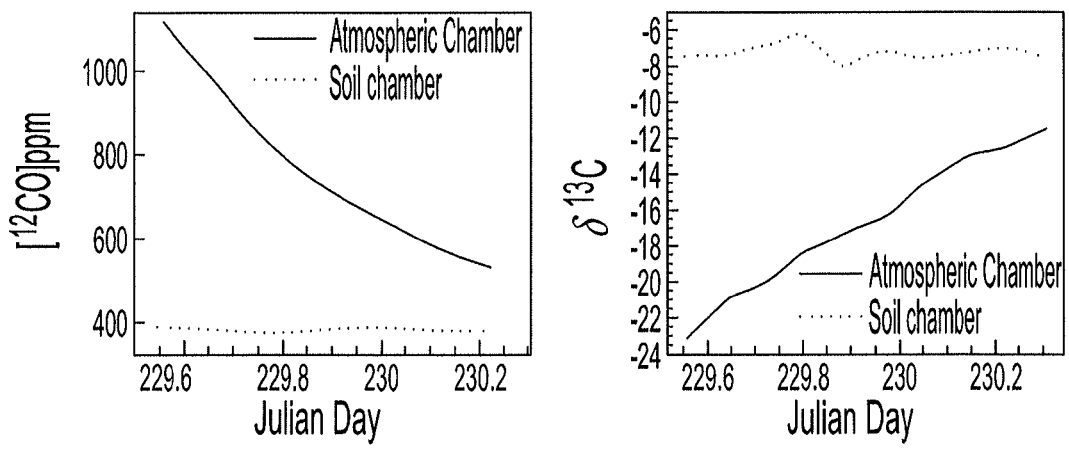
Fig-8C
Fig-8D

US 8,681,336 B2

SYSTEM AND METHOD FOR DETERMINING FLUX OF ISOTOPOLOGUES

FIELD

Exemplary embodiments described herein relate to systems and method for determining properties of soil efflux.

INTRODUCTION

The measurement of stable carbon isotopes has become a critical tool in elucidating the biological and environmental controls on many of the pathways by which $CO_2$ can be produced and emitted from the soil.

SUMMARY

The embodiments described herein provide in one aspect a method for determining flux of a component of a gas of interest, the method comprising: placing a first chamber having an open bottom sealably in contact with a soil location, the first chamber being in communication with the soil via an inlet membrane covering the open bottom and being in communication with atmosphere surrounding the first chamber via one or more outlet membranes; after allowing gas in the first chamber to reach equilibrium, measuring a first concentration of a first isotopologue of the gas of interest within the first chamber and a first concentration of a second isotopologue of the gas of interest within the first chamber; placing a second chamber having a closed bottom in a vicinity of the first chamber, the second chamber being in communication with the surrounding atmosphere via one or more outlet membranes of the second chamber, measuring the atmospheric concentration of the first isotopologue within the second chamber after allowing gas in the second chamber to reach equilibrium and measuring the atmospheric concentration of the second isotopologue within the second chamber after allowing gas in the second chamber to reach equilibrium; and determining a flux of the first isotopologue through the inlet membrane relative to a flux of the second isotopologue through the inlet membrane.

The embodiments described herein provide in another aspect a system for determining flux of a component of a gas of interest comprising:

a first chamber comprising chamber walls and a lid defining a first cavity having a first size and shape, the chamber walls also defining an opening for sealably contacting the cavity with a soil location, the first chamber walls further defining one or more first outlet openings providing communication between the cavity and atmosphere surrounding the first chamber; the first chamber further comprising an inlet membrane covering the opening having an inlet membrane diffusivity and one or more first outlet membranes covering the one or more first outlet openings having a lower diffusivity than the inlet membrane diffusivity;

a second chamber comprising chamber walls and a lid defining a second cavity having a height and width substantially equal to the shape and size of the first cavity, the chamber walls further defining one or more second outlet openings being shaped and sized substantially equal to the one or more first outlet openings, the one or more second outlet openings providing communication between the second cavity and atmosphere surrounding the second chamber, the second chamber further comprising one or more second outlet membranes covering the one or more second outlet openings having a diffusivity substantially equal to the diffusivity of the one or more first outlet membranes; and one or more measuring devices for measuring a first concentration of a first isotopologue of the gas of interest within the first cavity, a first concentration of a second isotopologue of the gas of interest within the cavity, an atmospheric concentration of the first isotopologue of the gas of interest within the second cavity and an atmospheric concentration of the second isotopologue of the gas of interest within the second cavity.

Further aspects and advantages of the embodiments described will appear from the following description taken together with the accompanying drawings.

DRAWINGS

These and other features of exemplary embodiments will become more apparent from the following in which reference is made to the appended drawings wherein:

FIG. 7 is a graph showing the absolute probable error in calculated isotopic flux value.

FIGS. 8a-8d are graphs showing the observe decal in isotopologues.

DESCRIPTION OF VARIOUS EMBODIMENTS

When measuring soil gas efflux and its stable isotopic signature, chamber methods, such as those using static or dynamic chambers, may drive a potentially large bias because of non-steady state diffusion processes. These biases are likely to co-vary with environmental conditions, thereby confounding the interpretation of results further. Such methodological biases have been documented and some solutions have been offered, such as modification of conventional chamber designs to minimize the bias, and model fitting of the chamber to remove bias artifacts. Although each of these approaches is likely to offer data that is somewhat more reliable, it is desired to have ways for measurement that have a lower risk of bias.

A steady-state chamber system and method called Forced Diffusion are herein described for use in the measurement of isotopic fluxes. Steady state diffusion based chamber design seeks to address the issue of bias in the measurement of isotopic fluxes.

Exemplary embodiments described herein refer to the measurement of gas fluxes and isotopic fluxes with reference to $CO_2$, $^{12}CO_2$ and $^{13}CO_2$, such reference is by way of example only. It will be understood that systems and method described may be applied to other gases of interest.

Chamber Design

Figure 1:
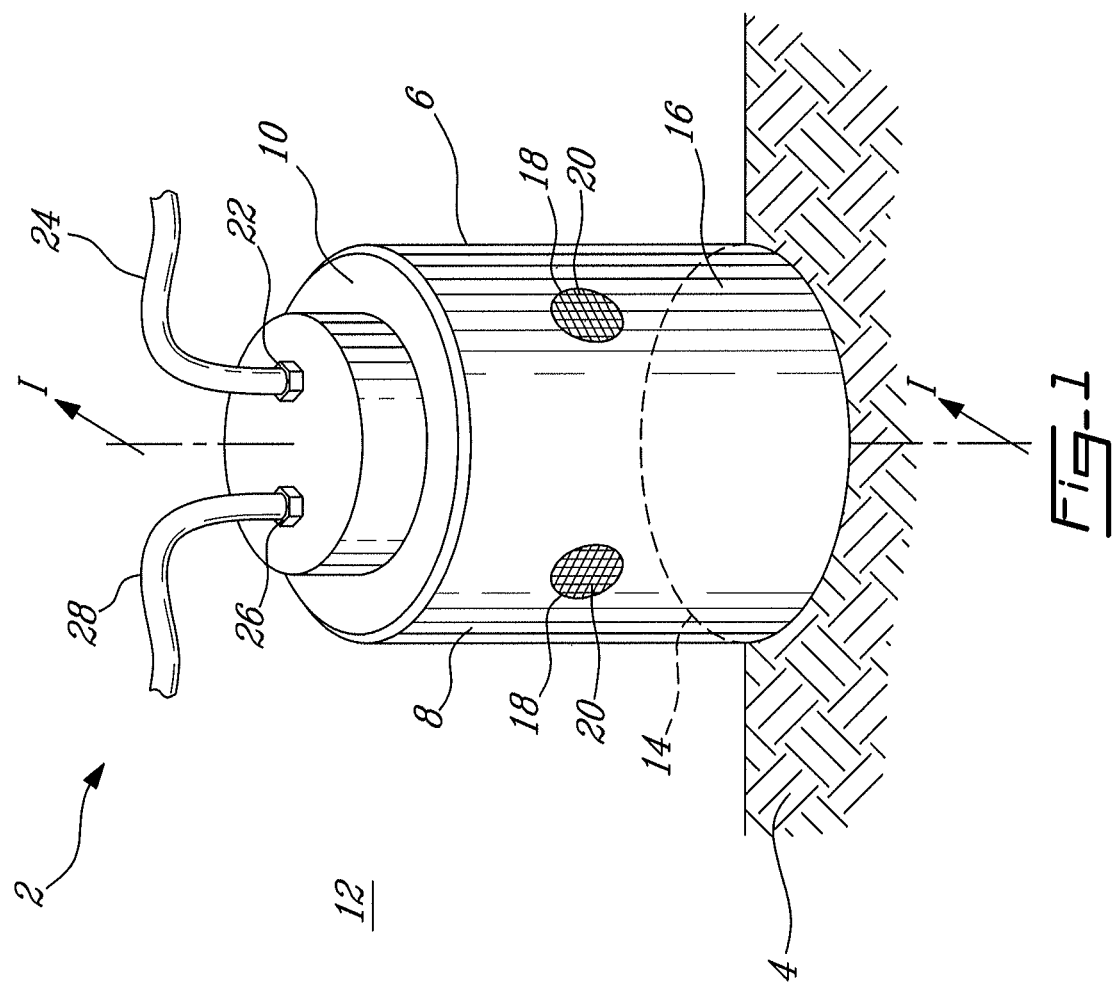
FIG. 1 is a perspective view of an isotopic forced diffusion chamber.
Figure 2:
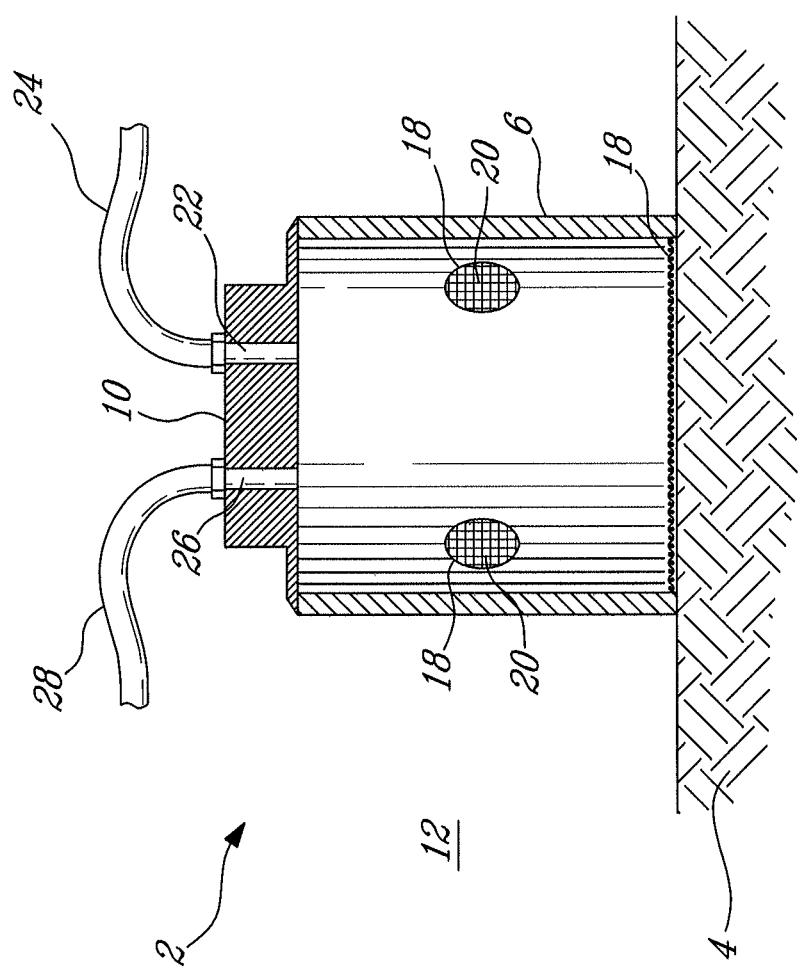
FIG. 2 is a section view of the isotopic forced diffusion chamber.

Referring to FIG. 1, therein illustrated is a perspective view of an exemplary isotopic forced diffusion chamber 2 (iso-FD chamber). FIG. 2 illustrates a section view of the exemplary isotopic forced diffusion chamber 2 along the line I-I. The iso-FD chamber 2 is shown as placed in a field location upon the soil 4. The iso-FD chamber 2 comprises chamber walls 6 which define a cavity 8. The chamber walls are formed of a non-permeable or low-permeability material. In some exemplary embodiments, the chamber walls may be formed of polyvinyl chloride (PVC).

A top portion of the cavity 8 is sealed by a lid 10 formed of a non-permeable or low-permeability material such that communication between the cavity 8 and the atmosphere surrounding the iso-FD chamber 2 is substantially restricted or prevented. In the embodiments where the chamber walls 6 are formed of PVC, the lid 10 may be a PVC plug. Alternatively the lid 10 may be integrally formed with the chamber walls 6.

In some exemplary embodiments, lid 10 may be selectively opened to allow communication of the cavity 8 with the surrounding atmosphere 12 through the top portion of iso-FD chamber 2. It may be desirable to open the lid 10 to allow vegetation within the cavity 8 to be exposed to elements of nature, such as air, water, and sunshine between taking of measurements of isotopic concentrations in the cavity 8. Thus, a lid-opening mechanism may be attached to the lid 10 to allow automatic control of the opening and closing of lid 10.

The chamber walls 6 define a bottom opening 14. The iso-FD chamber 2 may be placed such that the bottom opening 14 is sealably in contact with the soil. When so placed, the cavity 8 is in communication with the soil 4 through the bottom opening 14.

In some exemplary embodiments, the bottom opening 14 may be covered by an inlet membrane 16 having a known diffusivity for different gases and various isotopologues of each of the gases. Accordingly, the cavity 8 is in communication with the soil 4 through the inlet membrane 16 such that soil gas permeating through the inlet membrane 16 is diffused through the cavity 8. In some embodiments, the inlet membrane 16 is formed of UV resistant Tyvek™ material.

The chamber walls 6 further define one or more outlet openings 18, which are each covered by outlet membranes 20 having known diffusivities for different gases and various isotopolgues for each of the gases. Accordingly, the cavity 8 is in communication with the surrounding atmosphere 12 through the outlet membranes 20 covering the outlet openings 18.

After a period of time, as gases permeate from the soil 4 into the cavity 8 through the inlet membrane 16 being diffused by the inlet membrane 16, and as they permeate to and from the cavity 8 and the surrounding atmosphere 12, diffusion of gases in the cavity 8 will reach a steady-state, or equilibrium. When in this diffusive steady state, the concentration of a particular gas of interest, such as $CO_2$ and its isotopologues will be measurable. As will be appreciated, the time for reaching the steady state is a function of the size, shape and diffusivity of the inlet membrane 16 and the size, shape and diffusivity of the outlet membranes 20.

Described below, a critical factor in the accuracy of determination of flux of isotopologues is the ratio between the $^{12}CO_2$ concentration in the Iso-FD chamber 2, and concentration in the atmosphere (Chamber/Atmosphere; $C_2/C_1$). There is also a smaller error that is induced by difference between the isotopic signature in the iso-FD chamber 2 and the atmosphere (Chamber/Atmosphere; $\delta_2/\delta_1$), as this difference becomes small the error is minimized. For example, FIG. 7 shows the absolute probable error in the calculated isotopic flux value for $C_2/C_1$ and $\delta_2$-$\delta_1$ with 1% and 5% uncertainty in measured concentration values and 0.5‰ and 1.0‰ uncertainty in measured isotopic signatures (i.e. analytical uncertainty).

Accordingly, the size, shape, and diffusivity of inlet membrane 16 of the iso-FD chamber 2 are selected such that concentration of isotopologues of the gas of interest in the cavity 8 can be built up to be within a preferred range. To decrease uncertainties and obtain accurate determination of isotopic flux, it is preferable that when the gases in the cavity 8 reach a diffusive steady state there will be a high concentration of the isotopologues of the gas of interest to be measured in relation to the concentration of the same isotopologues of the gas of interest in the atmosphere. However, care should be taken such that the concentration of isotopologues of the gas of interest in the cavity 8 is not so high that isotopologues of the gas of interest cannot naturally flow from the soil ground 4 into the cavity 8. For example, too a high concentration in the cavity 8 may lead to drastically increased subsurface $CO_2$ concentrations below the chamber and may further cause shifts in the biology near the location of the iso-FD chamber 2.

Preferably, the diffusivity of the inlet membrane 16 is greater than the diffusivity of the outlet membranes 20 to allow buildup of a sufficiently high concentration of $CO_2$ within the cavity 8 so that isotopic measurements of different isotopic concentrations may be made with minimal error. For example, the outlet membranes may be formed of GORE-TEX™, which has a lower diffusivity than Tyvek™. Similarly, it is preferable to size and shape the outlet openings 18 to allow a build of a sufficiently high concentration of $CO_2$ within the cavity 8.

For example, according to one embodiment, the cavity 8 defined by the chamber walls 6 has a diameter of approximately 5 cm and a length of 8 cm. Two approximately 10 cm² outlet openings 18 are located in the chamber walls 6 to oppose each other. In some embodiments, outlet opening 18 may extend circumferentially around the chamber walls 6 at a height above the soil 4, depending on the size of the chamber to achieve a preferential concentration of isotopologues of the gas interest in the cavity 8.

A suitable measuring device 30 is used to measure concentration of various isotopologues of the gas of interest, such as $CO_2$, $^{12}CO_2$ or $^{13}CO_2$, within the cavity 8 once gases in the cavity 8 have reached a diffusive steady-state. According to some exemplary embodiments, the lid 10 may comprise an outlet port 22 that allows the drawing of gases found within the cavity 8 for measurement of concentration of isotopologues of the gas of interest. For example, outlet port 22 may be attached to an outlet tube 24 that is connected to an input port 32 of a measuring device 30.

One type of measuring device suitable for measuring concentration of isotopologues of the gas of interest is a cavity ring down spectrometer. In such cases, the outlet port 22 may be connected to an input of the cavity ring down spectrometer. For example, a Picarro™'s G1101-I CRDS™ analyzer may be used.

In some exemplary embodiments, the Iso-FD chamber may further comprise an inlet port 26, which allows for the insertion of air into the cavity 8. Such insertion of air may be useful for maintaining a substantially constant pressure within the cavity 8 to avoid biases in isotopologues of the gas of interest concentration measurements caused by fluctuations in pressure.

Figure 3:
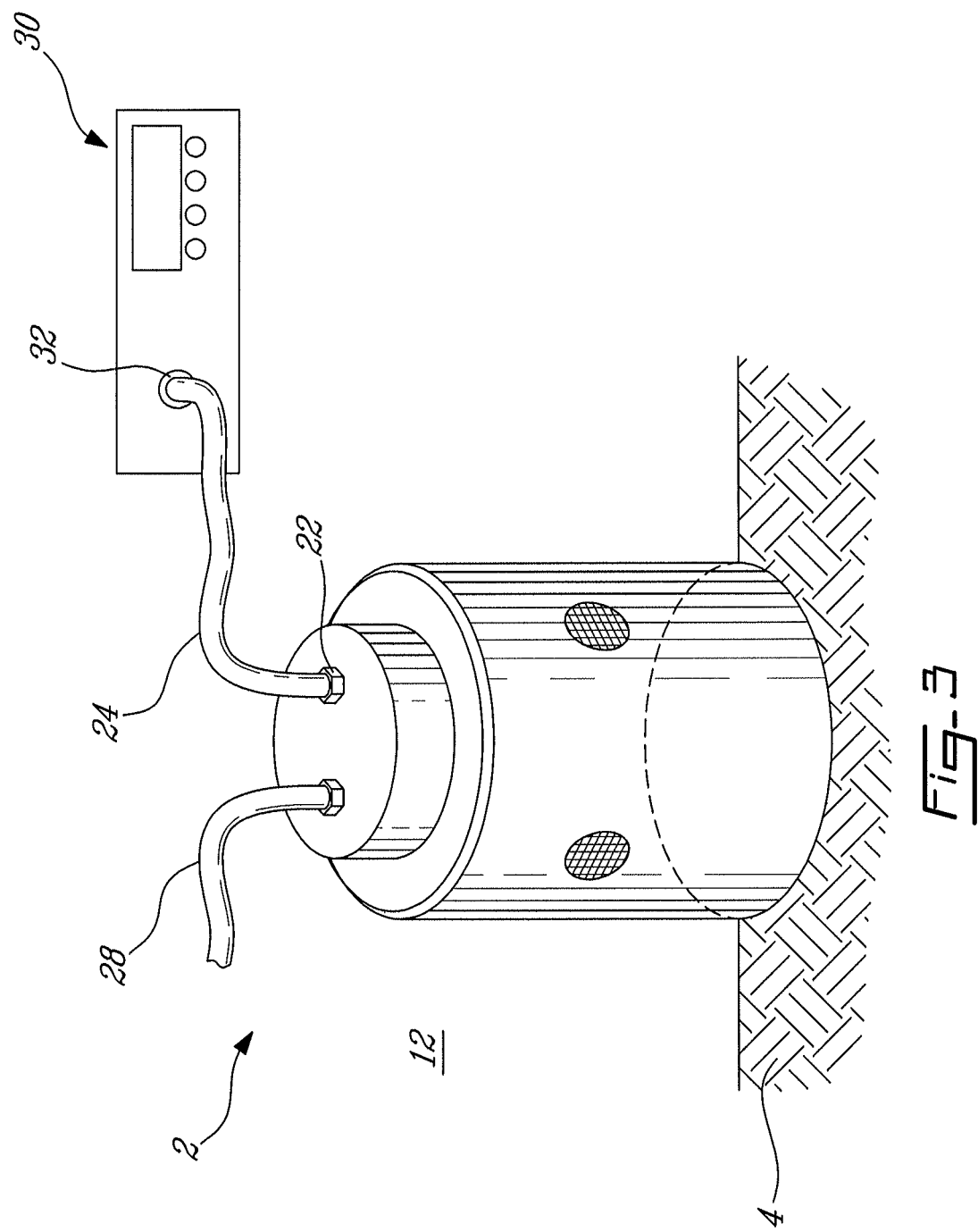
FIG. 3 is a perspective view of an isotopic forced diffusion chamber connected to a measuring device.

Referring to FIG. 3, therein illustrated is a perspective view of the iso-FD chamber 2 being connected to a measuring device 30 such as a cavity ring down spectrometer. In this exemplary embodiment, the outlet port 22 of the iso-FD chamber 2 is connected to an input 32 of the measuring device 30 by outlet tube 24. Inlet port 26 of the iso-FD chamber 2 is further connected to an inlet tube 28. One end of the inlet tube 28 is open and in communication with the atmosphere 12 surrounding the iso-FD chamber 2. The inlet tube 28 has a length that such that there is a significant concentration gradient over its length. Therefore diffusion of surrounding atmosphere 12 through the inlet tube 28 does not substantially affect concentration of soil gas in the cavity 8. However, when there is a change of pressure in the cavity 8, such as when cavity gases are drawn for measurement, the change in pressure in the cavity 8 causes air from the surrounding atmosphere 12 to be drawn into the cavity 8, thereby maintaining constant pressure.

Figure 4:
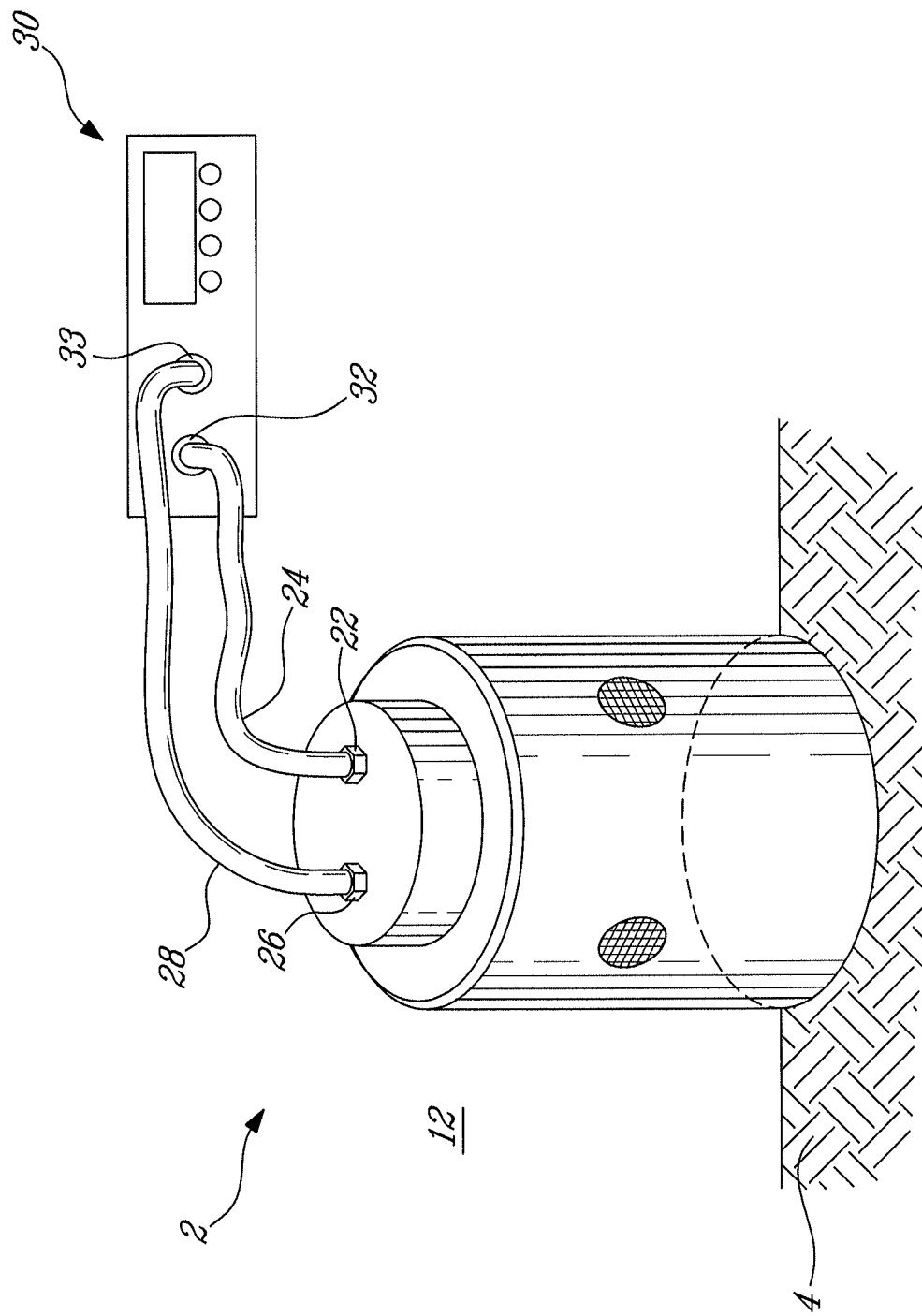
FIG. 4 is a perspective view of an isotopic forced diffusion chamber connected to a measuring device.

Referring now to FIG. 4, therein illustrated is a schematic view of an exemplary embodiment the iso-FD chamber 2 having the outlet port 22 being connected to an input port 32 of the measuring device 30 via the outlet tube 24. The inlet port 26 of the iso-FD chamber 2 is further connected to an output port 33 of the measuring device via the inlet tube 28. The measuring device 30, such as a spectrometer, is configured to circulate gas drawn from the cavity 8 through the outlet port 22 and input port 32 back into the cavity 8 through output port 33 of the measuring device 30 and inlet port 26. Preferably the drawing of gas from the cavity 8 and the reinsertion of gas back into the cavity 8 should be done continuously or almost continuously such that any gas drawn from the cavity 8 by the measuring device 30 is quickly reinserted back into the cavity 8. The continuous drawing of gas and reinsertion of gas creates a continuous flow loop of gas having a defined flow rate from cavity 8 to the measuring device 30, and back to the cavity 8. The continuous drawing and reinsertion of gas restricts disruption of gas pressure in the cavity 8 because any gas drawn from the cavity 8 by the measuring device 30 is offset by gas reinserted by the measuring device 30. As gas is drawn from the cavity 8, and before the gas is reinserted into the cavity 8, the measuring device 30 can measure the concentration of isotopologues of the gas of interest within the gas that is drawn. The flow rate of the continuous flow loop should be sufficiently high such that sufficient gas is drawn to obtain accurate measurements of isotopologues of the gas of interest, However, the flow rate should not be so high that the measuring device is unable to obtain accurate measurements or be above a maximum flow rate for which the measuring device 30 is capable of operating.

According to some exemplary embodiments, the iso-FD chamber 2 comprises a sampling port for receiving a sampling canister. Preferably, the sampling port is located on the lid 10 of the iso-FD chamber 2. The sampling port may comprise a valve to selectively open or close the port depending on whether a sampling canister is coupled to it. When a sampling canister, such as a gas canister or vial, is coupled to the sampling port, the valve may be opened to allow gas of the cavity 8 to enter the sampling canister. The sampling canister may then be brought for measurement and analysis. It will be appreciated that use of the canister in this way allows the sampling canister to be brought off-site from the location of the iso-FD chamber 2. For example, the sampling canister may be brought to a laboratory for in-depth analysis. According to such embodiments, either one or both of the inlet port 26 and outlet port 22 may be omitted from the iso-FD chamber 2. However, alternatively, it is possible for the iso-FD chamber 2 to have the sampling port in addition to the inlet port 26 and outlet port 22 such that an operator may choose between obtaining cavity gas measurements using a measuring device connected to the outlet port 22 or obtaining measurements using sampling canister attached to the sampling port.

According to some exemplary embodiments, the sampling canister may be a molecular sieve sampling can that is semi-automated using control hardware such as a flow measurement and control device. The control hardware may further include a pump with concentration sensors. The control hardware provides quality assurance in verifying that a sample has been drawn correctly and in large enough volume. The control hardware may also set the sample to be drawn at pre-selected time intervals. As the sampling port and sampling canister allow the gases in the cavity 8 to maintain equilibrium, samples can be repeatedly taken without having to reconfigure the chamber.

While some examples of the measuring device 30 have been provided, it is contemplated that other measuring devices may be used to measure concentration of isotopologues of the gas of interest in the cavity 8. For example, it is contemplated that in-cavity measuring devices may become available for easier measurements. Such devices are intended to be covered by the present description.

In some embodiments, the steady-state chamber system comprises at least one iso-FD chamber 2 and a reference chamber 50. The reference chamber 50 is used to measure concentration of isotopologues of the gas of interest in the atmosphere. This measurement is then used to determine the relative flux of isotopologues of the gas of interest. The reference chamber 50 is designed to be similar to the iso-FD chamber 2. In particular, the reference chamber 50 also comprises chamber walls that define a cavity having a diameter and length that is substantially equal to the diameter and length of the cavity 8 of the iso-FD chamber 2. The chamber walls of the reference chamber 50 are preferably also formed of the same material as the chamber walls 6 of the iso-FD chamber 2. A top portion of the cavity of the reference chamber 50 is also covered by a lid to seal the top portion of the cavity. Moreover the chamber walls of the reference chamber 50 also define one or more outlet openings that are each covered by outlet membranes. Preferably, the reference chamber 50 has the same number of outlet openings as the iso-FD chamber 2 and each of the outlet openings have the same shape and size as the outlet openings 18 of the iso-FD chamber 2.

Each of the outlet openings of the reference chamber 50 are covered by outlet membranes having a diffusivity substantially equal to the diffusivity of the outlet membranes 20 of the iso-FD chamber 2. However, importantly, the bottom opening of the cavity defined by the chamber walls of the reference chamber 50 is sealed with a non-permeable material, such that soil gases do not flow from the soil 4 into the cavity 8. By having a reference chamber 50 that has a similar configuration to the iso-FD chamber it is possible to closely monitor changes in the concentration of $CO_2$ in the atmosphere and correct for such changes in the flux determinations. Exemplary embodiments of the iso-FD chamber 2 described herein may also be applied to the reference chamber 50 where appropriate.

Figure 6:
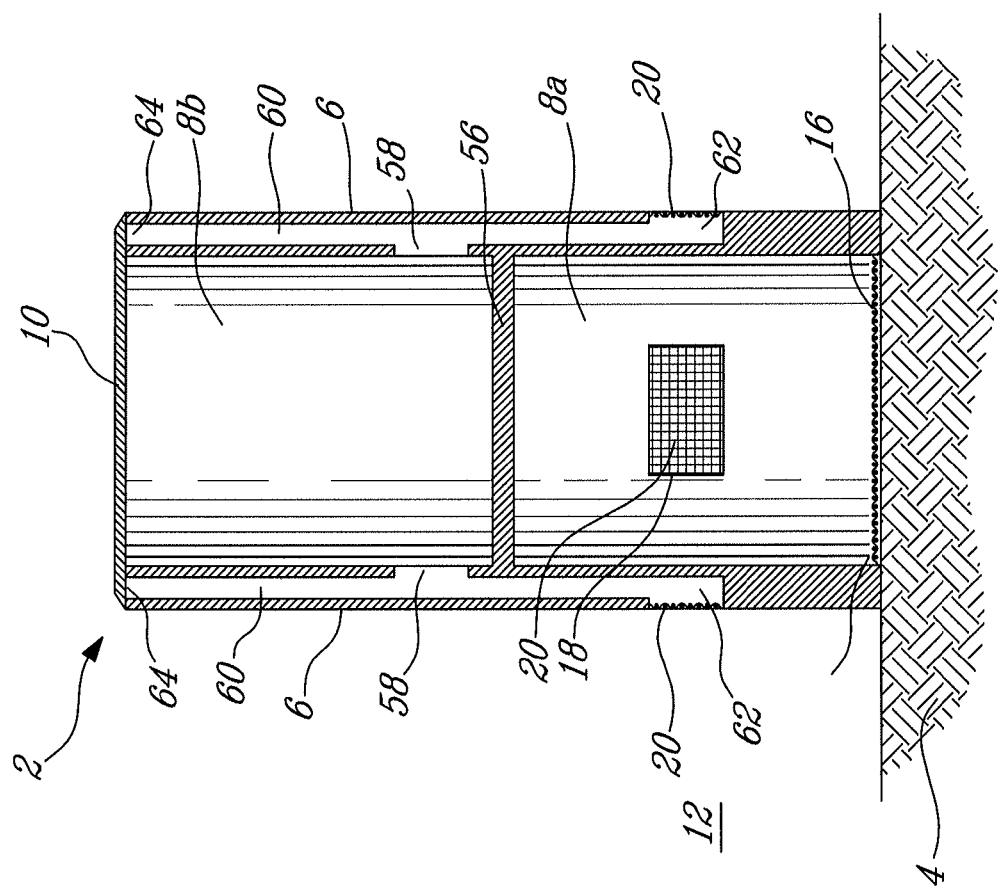
FIG. 6 is a graph showing errors for different gas concentration ratios.

Referring to FIG. 6, therein illustrated is a section view of the iso-FD chamber 2 and the reference chamber 50 being integrally formed according to some exemplary embodiments. Chamber walls 6 may be made to be approximately twice a high to define an enlarged cavity. The enlarged cavity is divided by lateral wall 56, which divides the enlarge cavity into soil sub-cavity 8a and reference sub-cavity 8b. Soil sub-cavity 8a is in communication with the soil 4 through bottom opening 14 being covered by inlet membrane 16. Chamber walls 6 further define outlet openings 18 being covered by outlet membranes 20 to provide communication between the soil sub-cavity 8a with the surrounding atmosphere 12. Reference sub-cavity 8b, being closed by lateral wall 56, is not in communication with soil 4. However, reference sub-cavity 8b is communication with the surrounding atmosphere 12 via reference sub-cavity recesses 58 defined on an inside surface of the chamber walls 6. The reference sub-cavity recesses connect to bores 60 drilled in the chamber walls 6. The bores 60 extend downwardly towards soil 4 to connect with recesses 62 defined on an outside surface of the chamber walls 6. The recesses 62 are further covered by outlet membranes 20. Therefore, sub-cavity 8b communicates with the surrounding atmosphere 12 via reference sub-cavity openings 58, bores 60 and recesses 62. Top openings 64 of the bores 60 are plugged to restrict communication of the reference sub-cavity 8b with the surrounding atmosphere through the top openings 64. The recesses 62 are located at a height above the ground approximately equal to the height of the outlet openings 18. Therefore, soil sub-cavity 8a, and reference sub-cavity 8b communicate with the surrounding atmosphere 12 at approximately the same points in space, thereby decreasing errors caused by lateral and vertical deviations in concentrations of the isotopologues of the gas of interest in the surrounding atmosphere 12. Measurements of concentrations of isotopologues of interest in the soil gas is obtained by measurement of concentrations of gas in the soil sub-cavity 8a. Reference concentrations of isotopologues of interest in the atmosphere is obtained by measurement of concentrations of gas in the reference sub-cavity 8b.

Measurements of concentration of isotopic fluxes in the cavity 8 of the reference chamber 50 may be carried out with the measurement device according to any of embodiments provided above with reference to the iso-FD chamber 2. To obtain accurate measurements and minimize errors caused by lateral deviations in concentration of isotopologues in the surrounding atmosphere 12, the reference chamber is preferably placed as close as possible to the iso-FD chamber 2. Furthermore, in some embodiments, the iso-FD chamber 2 is connected to a first measuring device 30 while the reference chamber 50 is connected to a second measuring device 30 that is separate from the first measuring device. However, a single measuring device 30 may be used to measure concentrations of isotopologues of the gas of interest in both the iso-FD chamber 2 and the reference chamber 50.

Figure 5:
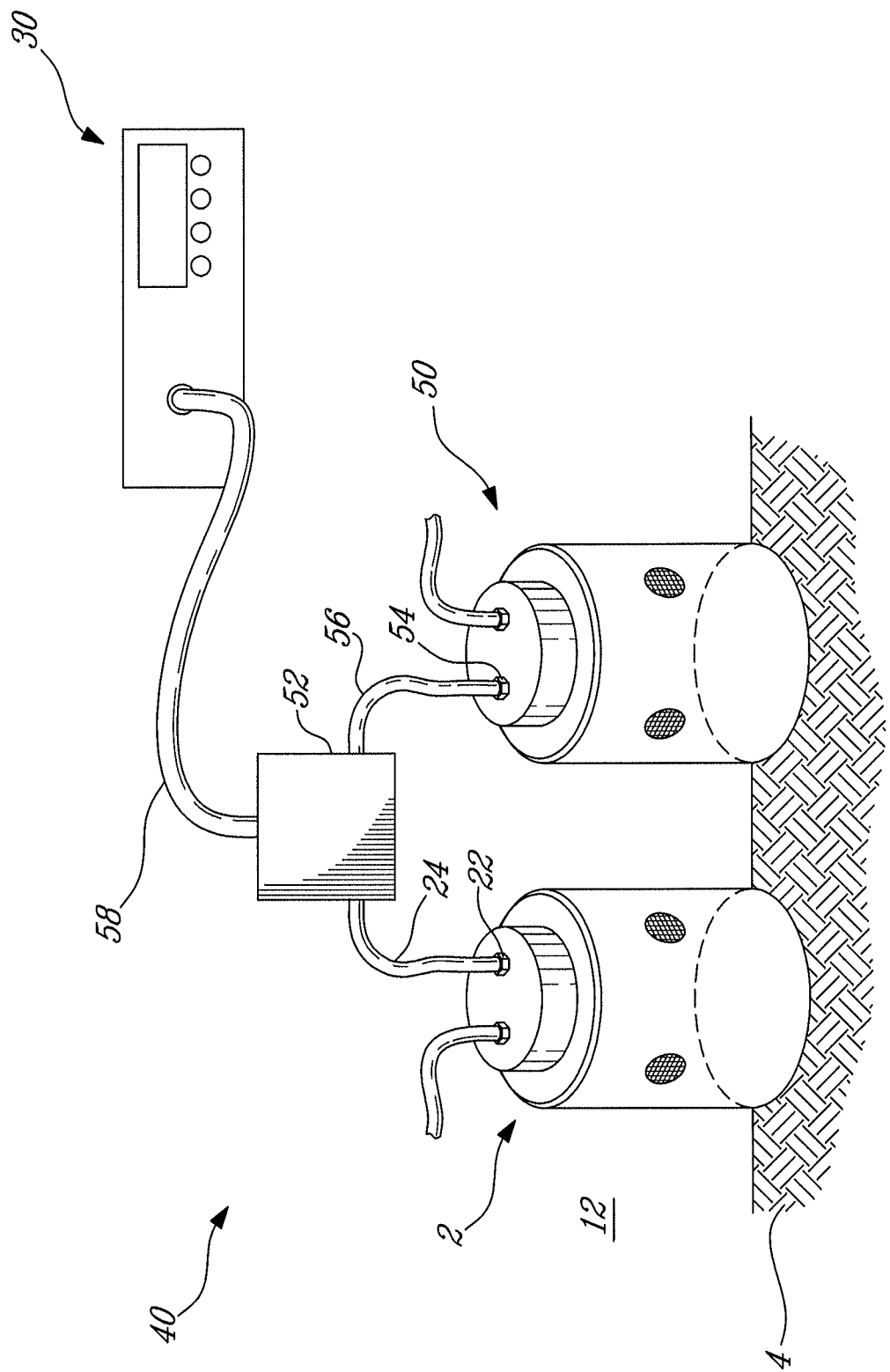
FIG. 5 is a perspective view an isotopic forced diffusion chamber and a reference chamber connected to a measuring device.

Referring now to FIG. 5, therein illustrated is an exemplary embodiment of the iso-FD chamber system 40 comprising a valving system for taking bulk measurements of concentration of isotopologues of the gas of interest in a plurality of chambers. For example, iso-FD chamber system 40 comprises one iso-FD chamber 2 and a reference chamber 50 positioned in proximity to one another. Cavity 8 of the iso-FD chamber 2 sealably contacts the soil 4 such that soil gases permeate into cavity 8 through inlet membrane 16. Inlet port 26 is connected via inlet tube 28 to a valving system 52. Inlet port 54 of reference chamber 50 is connected via inlet tube 56 to the valving system 52. The valving system 52 is further connected to an input port 32 of the measuring device 30 via connecting tube 58. The valving system 52 comprises a plurality of valves and interconnecting tubes.

The valving system 52 allows measurements of isotopologues of the gas of interest found in a plurality of chambers to be taken using a measuring device 30 having a single input port, such as a spectrometer Picarro™'s G1101-i CRDS™ analyzer is factory equipped with a single inlet port. The valving system 52 may comprise eight EV-2M two-way valves connected to a gas tight manifold. Two of these valves are dedicated to standard gases, while the other 6 are free to collect samples. The valves are fired using a PhidgetInterfaceKit 0/0/8 electronic relay (Phidgets Inc., Calgary, Alberta), which is connected to a Picarro™ G1101-i CRDS™ and is commanded by a controller. Accordingly, the controller can selectively control the valving system to connect the input port 32 of the measuring device 30 with the outlet ports of either the iso-FD chamber 2 or the reference chamber 50.

The controller may also control the lid opening mechanism of lid 10 to selectively open the lid after taking a measurement of concentration of isotopologues and to selectively close the lid when another measurement of concentration of isotopologues is to be taken. The controller may further be configured to receive measurements of concentrations of isotopologues taken by the measuring device and to determine the flux of one isotopologue of the gas of interest relative to the flux of another isotopologues of the same gas of interest. Furthermore, the controller may further be configured to control actions carried out by the measuring device 30 such as the taking of measurements of concentrations of isotopologues, the drawing of gas for measurement, the reinsertion of gas into the cavity 8, and the control of sample port valve in some embodiments. The controller may further be coupled to a display unit and data input device, such as keyboard or mouse, for entering various parameters, such as membrane diffusivities.

The controller described herein may be implemented in hardware or software, or a combination of both. It may be implemented on a programmable processing device, such as a microprocessor or microcontroller, Central Processing Unit (CPU), Digital Signal Processor (DSP), Field Programmable Gate Array (FPGA), general purpose processor, and the like. In some embodiments, the programmable processing device can be coupled to program memory, which stores instructions used to program the programmable processing device to execute the controller. The program memory can include non-transitory storage media, both volatile and non-volatile, including but not limited to, random access memory (RAM), dynamic random access memory (DRAM), static random access memory (SRAM), read-only memory (ROM), programmable read-only memory (PROM), erasable programmable read-only memory (EPROM), electrically erasable programmable read-only memory (EEPROM), flash memory, magnetic media, and optical media. The controller may be implemented within the measurement device 30.

According to some exemplary embodiments, the controller may be implemented as a module within the measurement device. Alternatively, the controller may be implemented independently of the measuring device 30, but may be in communication with the one or more measuring devices 30. In such embodiments, some control steps may be implemented using the independently implemented controller while other control steps herein described are implemented by the measuring device 30.

In some exemplary embodiments, the iso-FD chamber system may comprise any number of iso-FD chambers 2 to take measurements of isotopic soil flux at multiple locations. Each outlet port 22 of the iso-FD chambers 2 can be connected to a valving system 52, which is further connected to the input ports 32 of one or more measuring devices 30. According to such embodiments, it is possible to automatically take bulk measurements of concentration of isotopologues of the gas of interest in each of the multiple iso-FD chambers 2 and subsequently calculate the relative gas flux at multiple soil locations. In some exemplary embodiments, multiple iso-FD chambers 2 may be used in order to simultaneously determine isotopic flux of a gas of interest at multiple soil locations. It may be sufficient to have one reference chamber 50 to obtain reference measurements of concentration of isotopologues of the gas of interest in the atmosphere. However, where the iso-FD chambers 2 are sufficiently spread out in area over various soil locations, multiple reference chambers 50 may be used. Each iso-FD chamber 2 is then associated with one of the reference chambers 50 that is in its vicinity. It will be understood that more than one iso-FD chambers 2 may be associated with a single reference chamber 50. Depending on the total number of chambers, one or more measuring devices 30 may be used to measure concentration of isotopologues of a gas of interest in each of the chambers. For example, two or more chambers may be connected to one measuring device 30 via the valving system 52. Advantageously, iso-FD chambers 2 that are associated with the same reference chamber 50 are connected via valving system 52 to the same measuring device 30 with the reference chamber 50. The controller may be configured to selectively control the valves of the valving system 52 to allow the measuring device 30 to sequentially measure concentration of isotopologues of the gas of interest. For example, the measuring device 30 and the valving system 52 may be controlled so that measurement of concentration of isotopologues in one iso-FD chamber 2 and measurement of concentration of isotopologues in the associated reference chamber 50 are taken within a short time of each other. Preferably, measurements should be taken at substantially the same time. Alternatively, where an iso-FD chamber 2 and its associated reference chamber 50 are connected to separate measuring devices, the measuring devices 30 may be controlled to take measurements of concentration of isotopologues in the iso-FD chamber 2 and measurement of concentration of isotopologues in the associated reference chamber 50 at substantially the same time.

In some exemplary embodiments, the iso-FD chamber 2 may further comprise a sensor for measuring concentration of a bulk gas of interest, such as $CO_2$, without specifically measuring the isotopologues of that gas. Accordingly, a measuring device 30 may still be used to measure the concentration of isotopologues of the gas of interest. However, it is contemplated that the same sensor may be used to measure both the concentration of the bulk gas as well as isotopologues of that gas. Measurements of the concentration of the bulk gas may be useful for monitoring changes in carbon balance of gases in the iso-FD chamber 2. According to such embodiments, the iso-FD chamber 2 may be configured, for example, by varying the size of the cavity walls, size of outlet openings, and outlet membrane diffusivity, such that a lower concentration of soil gas is found in the cavity 8 when diffusive equilibrium reached. Because more significant errors are introduced for measurements of concentration of bulk gas when there is a higher concentration of that gas, it may be desirable when measuring both bulk gas and isotopologues of that gas to have a concentration of soil gas that is lower than the concentration of soil gas when only concentrations of isotopologues are to be measured. However, the concentration of the soil gas is still maintained to be sufficiently high to obtain accurate measurements of concentrations of isotopologues.

Theory

While not being bound in any way, the inventors propose the following theoretical basis. The theory presented herein relates to $CO_2$ and its isotopologues, however it will be understood that such theory can be applied to any other gases and isotopologues of such gases. For the iso-FD chamber 2, the mass balance for bulk $CO_2$ measurements may be calculated as:

$$V\frac{\partial C}{\partial t} = A_B F_{in} - A_T F_{out} \quad (1)$$

where V is the cavity 8 volume, C is concentration, t is time, $A_B$ is the area of the inlet membrane in contact with the soil surface, $F_{in}$ is the flux into the cavity 8 and $A_T$ is the area of the outlet membranes 20 in contact with the atmosphere, $F_{out}$ of the chamber can be thought of as the diffusive gradient across the membrane from the concentration in the chamber C(t) to the concentration in the atmosphere $C_{atm}$, which is dependent on both the path length of diffusion (L) and the diffusivity of the membrane material (D), as per Fick's Law. With these substitutions for $F_{out}$, the equation can be modified to:

$$V\frac{\partial C}{\partial t} = A_B F_{in} - A_T \frac{D}{L}(C(t) - C_{atm}) \quad (2)$$

Since measurements are taken when the diffusion of gases in and out of the iso-FD chamber 2 is at equilibrium, it is approximated that diffusion through the chamber has reached steady-state. Equation may be reduced to:

$$F_{in} = \frac{A_T}{A_B}\frac{D}{L}(C_{FD} - C_{atm}) \quad (3)$$

Equation 3 describes the soil flux, where the atmospheric $CO_2$ concentration, $C_{atm}$ is subtracted from the $CO_2$ concentration in the chamber, $C_{FD}$. $C_{atm}$ is measured in the reference chamber 50 having a non-permeable bottom.

In the case of isotopic flux, each of the carbon isotopologues of $CO_2$ is treated as separate diffusing gases, which allows for the writing of similar equations for both $^{12}CO_2$ and $^{13}CO_2$. By taking the ratio of the fluxes of each isotopologues the isotopic composition of soil flux is gained:

$$\frac{F_{in}^{13C}}{F_{in}^{12C}} = \frac{\frac{A_T}{A_B}\frac{D^{13C}}{L}(C_{FD}^{13C} - C_{atm}^{13C})}{\frac{A_T}{A_B}\frac{D^{12C}}{L}(C_{FD}^{12C} - C_{atm}^{12C})} \quad (4)$$

which can be simplified based on the understanding that 1) the area variables will cancel because the same chamber is used for each isotope, and 2) the path length (L) and diffusivity will reduce to the reciprocal of diffusion fractionation (1.0044) yielding the final Iso-FD solution:

$$\frac{F_{in}^{13C}}{F_{in}^{12C}} = \frac{1}{1.0044}\frac{(C_{FD}^{13C} - C_{atm}^{13C})}{(C_{FD}^{12C} - C_{atm}^{12C})} \quad (5)$$

Equation 5 can be converted to del-notation for more convenient use.

As described above Isotopologues concentration within the cavity 8 of Iso-FD chamber 2 may be measured using a measuring device such as a cavity ring down spectrometer connected to outlet port 22 of the Iso-FD chamber 2 via outlet tube 24. As described above, according to some embodiments, the chamber gas can be continuous flow loops to allow gas to be recirculated to maintain the steady-state concentration within the chamber (as in Equation 2)

According to some other embodiments, gas can be drawn from the cavity 8 while volume replacement via the inlet tube 28. According to such embodiments, maintenance of pressure in the measurement cell of the measuring device relies on a difference between inflow and outflow rates and because of this recirculation would cause undesired pressure changes in the Iso-FD chamber and likely lead to biased results because of over/under pressurization in the cavity 8. Therefore, according to embodiments where air is drawn from the cavity 8 of the iso-FD chamber 2 and air of the surrounding atmosphere 12 flows in to the cavity 8 via an inlet tube 28 and replace air drawn by the measuring device, the original mass balance equation (Eq. 2) should be modified to:

$$V\frac{\partial C}{\partial t} = A_B F_{in} - A_T \frac{D}{L}(C(t) - C_{atm}) + \Gamma(C_{atm} - C(t)) \quad (6)$$

where $\Gamma$ is the measuring device pump draw rate (m³/s). To determine what effect the pump draw and atmospheric air dilution will have on the final calculation of the isotopic flux Equation 6 is solved analytically assuming that $F_{in}$ is constant. As the analytically modeled chamber air is drawn by the measuring device the concentration decays until it reaches an equilibrium value between the incoming atmospheric air (modeled at 380 ppm) and the soil flux rate into the chamber. Further analysis shows that for a fixed total pumping time, the difference between the isotopic flux determined using the steady-state Iso-FD and the pump drawn Iso-FD is always a constant value, regardless of the $F_{in}$ flux rate or the isotopic signature of the flux. This allows for the determination of an offset value for a given design of the iso-FD chamber 2 and applies it to the Iso-FD solution (Eq. 5) to correct it for the pump effects.

Numerical Modeling

To ensure that the Iso-FD chambers do not suffer from any of the lateral diffusion artifacts present in other chamber systems, the chambers were modeled using a three-dimensional soil-atmosphere-chamber model. This new model has cubic grid geometry, making it more flexible to use both for varying soil properties and varying chamber sizes and geometries. In brief, the model transports gas between its six nearest-neighbor cells using Fick's Law:

$$F_{1,2} = -D_{1,2} \frac{\Delta C_{1,2}}{\Delta(i,j,k)_{1,2}} \quad (7)$$

where F is the flux between cells, D is the intercell diffusivity constant, $\Delta C$ is the difference in the cell gas concentrations and $\Delta(i,j,k)$ is the three-dimensional difference in cell positions. After each time step, the concentrations in each cell are re-calculated taking into account relevant fluxes during the last time step. To this end, steady state chamber concentrations and isotopic signatures for diffusivities and production rates spanning three orders of magnitude ($D_{soil}$: $1 \times 10^{-8}$-$1 \times 10^{-6}$ m² s⁻¹; Production (P): 0.1-10 μmol m⁻² s⁻¹) were simulated, as well as several values for the diffusivity of the Iso-FD chamber membrane (D term in Equation 3). The modeled and actual chamber had similar surface areas (Modeled: $A_T = A_B = 16$ cm² Actual: $A_T = 20$ cm², $A_B = 19$ cm²) although the volume of the modeled system was about half for computational reasons (Modeled V=64 cm³ Actual V=133 cm³);

however, this difference in V does not affect the final model results. For each combination of parameters ($D_{soil}$, P, D) the true isotopic flux of the modeled soil was compared to the flux estimated using the modeled Iso-FD chamber to estimate potential bias under the various conditions. It will be appreciated that dimensions of the system presented herein are given as examples only. Especially, where modeling is used to validate the system design, dimensions used for the modeling relate to only one embodiment, but other dimensions are contemplated.

Method

According to exemplary embodiments of a method for determining flux of a component of a soil gas in application of the theory described above, the iso-FD chamber 2 is placed at a soil location. When so placed, the bottom opening 14 is sealably in contact such that the cavity 8 is in communication with the soil 4 via the inlet membrane 16 covering the bottom opening. A collar having a first end inserted into the soil and a second end in contact with the bottom portion of the chamber walls 6 may be used to aid in the sealing of the bottom opening 14 to the soil 4. When so placed, the cavity 8 is further in communication with the surrounding atmosphere 12 via the one or more outlet membranes 20 covering the one or more outlet openings defined by the chamber walls 6.

A reference chamber 50 may also be placed at a soil location in order to obtain reference measurements of the surrounding atmosphere 12. Preferably, the reference chamber 50 is placed in the vicinity of the location of the first chamber 2 in order to obtain accurate reference measurements. Placing the reference chamber 50 in the vicinity of the iso-FD chamber 2 decreases errors that may be introduced due to horizontal differences in concentration of isotoplogues. When so placed, the cavity of the reference chamber 50 is in communication with the surrounding atmosphere 12 via one or more outlet membranes of the reference chamber 50 covering the one or more outlet openings defined by the chamber walls.

The iso-FD chamber 2 is placed for a waiting time $\Delta t_1$ to allow soil gases permeating and diffusing into the cavity 8 and gases 8 diffusing in and out of the cavity 8 through the one or more outlet membranes 20 to reach steady-state or equilibrium. For example it is possible to estimate the time needed for gas to reach equilibrium based on the known diffusivity of the outlet membranes 20, the known diffusivity of the inlet membranes, or a combination thereof. Modeling and validation in may be further used to verify the estimated time to equilibrium.

The reference chamber 50 may also be placed for a waiting time $\Delta t_2$ to allow soil gases permeating and diffusing in and out of the cavity 8 through the one or more outlet membranes to reach steady-state or equilibrium. Where the outlet openings 18 of the iso-FD chamber 2 and the outlet openings of the reference chamber are equal in quantity and have substantially the same shapes and sizes, and the outlet membranes covering the openings have the same diffusivity, the waiting time $\Delta t_2$ for the iso-FD chamber 2 and the waiting time $\Delta t_2$ for the reference chamber may be approximately equal.

After allowing gas in the iso-FD chamber 2 to reach equilibrium, a measurement is taken using the measuring device of the concentration of a first isotopologue of the gas of interest in the cavity 8 of the iso-FD chamber 2 and a measurement is taken of the concentration of a second isotopologue of the gas of interest in the cavity 8 of the iso-FD chamber 2. Preferably, the measurement of the first isotopologue and the second isotopolgue are measured at the same time, or as closely in time to each other as possible to minimize the time elapsed between measurements that could affect the accuracy of the formula used for determination of the relative flux. In some embodiments where flux of $CO_2$ gas is to be determined, the first isotopologue of the gas of interest may be $^{12}CO_2$, and the second isotopologue of the gas of interest may be $^{13}CO_2$, however measurements of any other isotopologue of the gas of interest may be taken.

Atmospheric concentrations of the first and second isotopologues of the gas of interest may be measured using the reference chamber 50. After allowing gas in the reference chamber 50 to reach equilibrium, a measurement is taken using the measuring device of the concentration of the first isotopologue of the gas of interest in the cavity of the reference chamber and a measurement is taken of the concentration the second isotopologue of the gas of interest in the cavity of the reference chamber 50. Since the reference chamber 50 has a closed bottom and therefore does not receive a substantial amount of soil gases, these measurements represent concentrations of the first and second isotopologues of the gas of interest in the atmosphere. The same first and second isotopologues of the gas of interest are measured in the iso-FD chamber 2 and the reference chamber 50.

Preferably, the measurements of isotopologues of the gas of interest in the iso-FD chamber 2 and the measurements of the isotopologues of the gas of interest in the reference chamber 50 should be undertaken closely together in time. Doing this allows for minimization of inaccuracies that may be introduced by changes in the surrounding atmosphere or soil gas over time.

According to some exemplary embodiments, the iso-FD chamber 2 may be connected to an input port 32 measuring device 30 via the outlet port 22 and outlet tube 24. Alternatively, the iso-FD chamber 2 may be connected to the input port 32 via the outlet port 22 and a valving system that is connected to the measuring device 30. In both cases, replacement of gas drawn by the measuring device 30 in order to maintain substantially constant pressure in the cavity 8 is provided by an inlet port 26 and inlet tube 28 in communication with the surrounding atmosphere. Measurement of the first and second isotopologues in the cavity 8 is conducted by drawing gas from the cavity 8. The drawing of gas from the cavity 8 may be for a specified time interval such that a high concentration of soil gas may be analyzed. However, it will be understood that as gas is drawn from the cavity 8 by the measuring device 30, air from the surrounding atmosphere 12 is inserted via the inlet port 26 to replace the gas that is withdrawn. Therefore the specified time interval is sufficiently short such that only an amount of gas is drawn that would not lead to a significant drop in soil gas concentration due to the insertion of air from the surrounding atmosphere 12 through inlet port 26. According to some embodiments, the measuring device 30 may repeatedly and periodically draw gas from the cavity 8 to measure isotopologues of the gas of interest within the cavity 8. Preferably, the measuring device 30 is configured to wait a time interval between drawing of gas for measurements where the length of the time interval is sufficiently long for soil gas concentrations within the cavity 8 to build up again to a sufficiently high concentration.

Where the reference chamber 50 is configured similarly to the iso-FD chamber 2, a similar method may be used for measuring the concentrations of isotopologues in the cavity of the reference chamber 50. Moreover, such measurements may be taken using the same measuring device 30 used for the iso-FD chamber 2, where both chambers are connected by a valving system 52. In such cases, the valves of the valving systems 52 are controlled such that the measurements of isotopologues in the iso-FD chamber 2 and the measurements of isotopologues within reference chamber 50 are taken as close in time as possible. Alternatively, each of the iso-FD chamber 2 and the reference chamber 50 are connected to separate measuring devices 30. In this case, the measuring devices are controlled to obtain measurements of isotopologues in the iso-FD chamber 2 and the reference chamber 50 at substantially the same time.

According to some exemplary embodiments, the iso-FD chamber 2 may be connected to an input port 32 of measuring device 30 via the outlet port 22 and further have inlet port 26 connected to an output port 33 of the measuring device. Accordingly, the connection of outlet port 22 and inlet port 26 of the iso-FD chamber creates a continuous loop through the input port 32 and output 35 of the measuring device. In this case, the measuring device 30 continuously draws gas from the cavity 8 of the iso-FD chamber via the outlet port 22 and input port 32. The continuously drawn gas spends a short amount of time in the measuring device 30 before the measuring device 30 ejects the gas through the output port 33 causing it to be reinserted into the cavity 8 through the inlet port 32. Therefore, as the measuring device 30 is continuously drawing gas from the cavity 8, it is also continuously reinserting gas into the cavity 8, thereby allowing maintenance of pressure within the cavity 8. The measuring device 30 may measure the first and second isotopologues of gas that pass through it when the gas is between the input port 32 and output port 33 of the measuring device 30 in the continuous flow of gas. According to some embodiments, the measuring device 30 may periodically and repeatedly measure the concentration of isotopologues of gas continuously passing through it. Where the reference chamber 50 is configured similarly to the iso-FD chamber 2, a similar method may be used for measuring the concentrations of isotopologues in the cavity of the reference chamber.

According to some exemplary embodiments, the iso-FD chamber 2 comprises a sampling port for receiving a sampling canister and a valve to selectively open or close the port. Accordingly, when a measurement is to be taken, a sampling canister is attached to the sampling port and the valve is controlled to be opened to allow gas in cavity 8 to enter the sampling canister. When the sampling canister is filled, the valve is controlled to be closed. The concentrations of isotopologues of a gas in the sampling canister may be automatically measured on-site or measured off-site, for example in a laboratory. Where concentrations of isotopologues in the sampling canister are measured automatically, such measurements may be repeatedly and periodically taken. Where the reference chamber 50 is configured similarly to the iso-FD chamber 2, a similar method may be used for measuring the concentrations of isotopologues in the cavity of the reference chamber 50. Moreover, the valve of the sampling port the iso-FD chamber 2 and the valve of the sampling port of the reference may be controlled to be opened at substantially same time to obtain samples of gas contained in both chambers.

According to some exemplary embodiments, the iso-FD chamber 2 comprises a lid that may be selectively opened and closed. Accordingly, after measuring the isotopologues of the gas of interest within the cavity 8, the lid 10 is opened to expose cavity 8 to the surrounding atmosphere 12 through the top opening 12. The lid 10 is left open for a time interval that is sufficiently long for vegetation in the cavity 8 to be exposed to the surrounding atmosphere 12 and elements of nature such as air, sunshine, rain, and other natural elements. To take a further measurement, the lid 10 is closed and a waiting time is allowed to pass such that the soil gases permeating into the cavity 8 and gas permeating in and out of the cavity 8 through the outlet membranes 20 are allowed to reach equilibrium. A further measurement of concentration of isotopologues of the gas of interest within the cavity 8 can then be taken. According to embodiments where measurements are repeatedly and periodically taken, the steps of taking a measurement, opening the lid, waiting a time interval, closing the lid, allowing gases to reach equilibrium are repeated for each measurement. Where the reference chamber 50 is configured similarly to the iso-FD chamber 2, a similar method may be used for measuring the concentrations of isotopologues in the cavity of the reference chamber.

According to some embodiments where the iso-FD chamber 2 further comprises a sensor for measuring concentrations of bulk gas, measurements of isotopologues of a gas and measurements of the bulk gas may be taken independently of each other.

After taking the measurements, the flux of the first isotopologues of the gas of interest from the soil ground 4 relative to the flux of the second isotopologues of the gas of interest from the soil ground 4 may be determined from the measured concentration of the first isotopologues of the gas of interest in the cavity 8, the measured concentration of the second isotopologues of the gas of interest in the cavity 8, the measured concentration of the first isotopologues of the gas of interest in the cavity of the reference chamber 50 and the measured concentration of the second isotopologues of the gas of interest in the cavity of the reference chamber 50. This determination of the relative flux is further based on the diffusivity of the first isotopologues of the gas of interest through the one or more outlet membranes 20 of the iso-FD chamber 2 and through the one or more outlet membranes of the reference chamber and on the diffusivity of the second isotopologues of the gas of interest through the one or more outlet membranes of the iso-FD chamber 2 and through the one or more outlet membranes of the reference chamber 50.

Where the outlet membranes 20 of the iso-FD chamber 2 and the outlet membranes of the reference chamber 50 have the same diffusivities, the flux may be determined according to the following equation, which is equivalent to the equation (5):

$$F_{rel} = \frac{D^{g1}\left(C_{FD}^{g1} - C_{atm}^{g1}\right)}{D^{g2}\left(C_{FD}^{g2} - C_{atm}^{g2}\right)}$$

wherein $F_{rel}$ is the flux of the first isotopologues of the gas of interest through the inlet membrane of the first chamber relative to a flux of the second isotopologues of the gas of interest through the inlet membrane of the second chamber, $D^{g1}$ is the diffusivity of the first isotopologues of the gas of interest through the one or more outlet membranes, $D^{g2}$ is the diffusivity of the second isotopologues of the gas of interest through the one or more outlet membranes, $C_{FD}^{g1}$ is the measured first concentration of the first isotopologue of the gas of interest within the iso-FD chamber 2, $C_{atm}^{g1}$ is the measured second concentration of the first isotopologue of the gas of interest within the iso-FD chamber 2, $C_{FD}^{g2}$ is the measured first concentration of the second isotopologue of the gas of interest within the reference chamber 50, and $C_{atm}^{g2}$ is the measured second concentration of the second isotopologue of the gas of interest within the reference chamber 50.

Determination of the relative flux may be made by the measuring device 30 where one device is used to measure concentration of the first and second isotopologues in both the cavity 8 of the iso-FD chamber 2 and the cavity of the reference chamber 50. Alternatively, a controller may be coupled to receive measurements from the measuring device, wherein the controller also performs determination of the relative flux. In some embodiments where multiple measuring devices are used to measure concentrations of first and second isotopologues in multiple iso-FD chambers 2 or reference chambers 50, the controller may receive measurements from each of the measuring devices and perform a determination of relative fluxes for each of the iso-FD chamber locations. Validation According to one exemplary embodiment of the system and method described herein a custom built Flux Generator (FG) was provided to test the design of the system and method. The FG is functionally similar to that of Martin and Bolstad[1], using most of the same operational parameters and mass balance equations for calculating flux. Within a 234.23 litre gas reservoir, a fan circulates injected gases at a fixed speed, mixing the whole volume in approximately 15 seconds. A 0.324 m² tray on top of the reservoir contains a homogenized synthetic "soil" of glass beads (22 cm deep). Concentrations of $CO_2$ in the gas reservoir are monitored continuously using a LiCor LI-820 infrared gas analyzer (IRGA). A four-port exhaust manifold and fan is situated over the tray to maintain the soil surface concentration near ambient levels, as described in Martin and Bolstad. A custom-designed LabVIEW interface and National Instruments Data Acquisition device automated the function of the FG (including $CO_2$ injections), performs calculations, and records data.

[1] Martin, J. G., Bolstad, P. V., 2003. "A carbon dioxide flux generator for testing infrared gas analyzer-based soil respiration systems." *Soil Society of America Journal* 68, at 514-518.

Within the FG glass bead soil two filtered sampling tubes were inserted, one near the top of the soil (about 2-3 cm deep) and one near the bottom of the soil (about 17-18 cm deep). These sampling tubes allowed for calculation of the true isotopic flux leaving the FG instrument so that the iso-FD chambers can be calibrated for the pump offset and also validate their ability to measure isotopic flux. Calculation of flux from these profile tubes uses the diffusion corrected two point Keeling plot approach.

An Iso-FD chamber and a modified Iso-FD chamber for atmospheric measurement (bottom surface sealed) were situated on the surface of the glass bead synthetic soil. The two soil profile tubes, two chambers, two atmospheric tubes, and two standards were all sampled for 15 minutes duration. The atmospheric tubes (in this case simply open to lab air) were sampled between soil profile and chamber measurements to ensure the sampling pathway was purged of any residual gases from the previous measurements.

Two separate laboratory trials of the Iso-FD method were performed on consecutive days. The FG was injected with $CO_2$ until the reservoir concentration reached 6000 ppm, after which time the gas was allowed to diffuse freely through the glass bead soil and into the lab atmosphere, with each run lasting approximately 15 hours.

Field Trial

According to one exemplary embodiment of the system and method described herein, iso-FD chambers were placed in a about 20 year old plantation of red pine (*Pinus resinosa*) located in Heatherton, Nova Scotia (N 45° 33'54", W 61° 46'20"). Annual average rainfall for the region is 1100 mm/year with average monthly rainfalls in August of 92 mm and 101 mm in September. Annual average temperature for the region is 7° C. and average temperatures in August and September are 18.9 and 15.3, respectively.

For a period of approximately 3 days, the Picarro™ G1101-i spectrometer was used to sample the two chambers (one iso-FD chamber and one reference chamber) as well was three horizontal soil gas well (about 4,13,26 cm depth) that were installed at the site in May 2011. The gas well was constructed using 50 cm long sections of 1.3 cm inside diameter PVC tubing. Holes (1.0 cm diameter) were drilled on opposing sides along the length of the pipe at ~4.5 cm intervals. The outsides of the wells were wrapped in Tyvek building material to exclude water from entering. An approximately 10 m long section of vinyl tubing was connected to the well via a barbed fitting to allow for sampling by the Picarro™ G1101-I spectrometer.

In a manner similar to the lab validation, described above the isotopic flux was calculated for the Iso-FD chambers (Equation 5) and compared to both the isotopic flux calculated via a two point Keeling plot approach using the shallowest subsurface gas well and the atmospheric $CO_2$ concentration and the isotopic signature of a 4-point Keeling plot that includes all three subsurface wells and the atmosphere.

Simulations of the Iso-FD method produced concentration and isotopic plumes directly below the chamber similar to those found using both static and dynamic chambers. However, in all simulations the predicted isotopic signature of flux using the Iso-FD method was very near the true value (True-Predicted; Mean Deviation<0.01‰). This quality may be attributed to the diffusive nature of the exchange of $CO_2$ with the surroundings. This allows the Iso-FD chamber to attain a new diffusive steady state during the measurement period that reflects the natural diffusive steady state and therefore allows the method to predict the true steady state value of flux, rather than a biased value.

Figure 9:
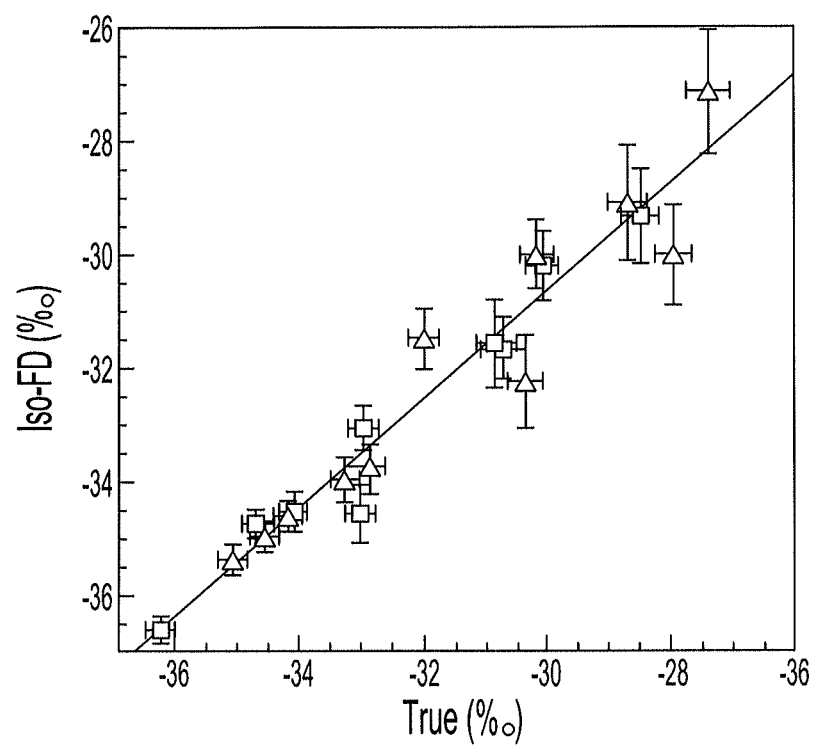
FIG. 9 is a graph of iso-FD measured isotopic flux values.

Two separate laboratory trials of one embodiment of the the Iso-FD method were carried out on consecutive days. The FG was injected with $CO_2$ until the reservoir concentration reached 6000 ppm, after which time the gas was allowed to diffuse freely through the glass bead soil and into the lab atmosphere, with each run lasting approximately 15 hours. FIG. 8a shows the observed decay in $^{12}CO_2$ concentrations in the glass bead soil, as measured by the soil profile tubes. To the right, in FIG. 87b is the trajectory of soil profile isotopic composition during the same time period. FIG. 8c shows the concurrent changes in the Iso-FD and atmospheric chamber $^{12}CO_2$ concentrations, with the isotopic signature of both chambers shown in FIG. 8d. Good correlation was observed between the "true" isotopic flux, calculated using the soil profile tubes, and the Iso-FD measured isotopic flux values, presented in FIG. 9. Linear regression results yielded a slope of 0.956 (S.E.=0.0575) and y-intercept of −1.958 (S.E.=1.848) with an $r^2$ value of 0.9322. This suggests that the desired offset for this particular Iso-FD chamber design (and measurement length) being 1.958‰, however the regression standard error is quite high leading to a large amount of uncertainty in the estimate. This large spread in the potential intercept value (−3.806 to −0.110) is due in part to the variability in the data and the large distance to extrapolate the curve to the y-axis. This may be constrained better by using injection gases with several different isotopic signatures (around 0‰ or heavier), although since the offset value is constant through time for a the same pump rate it will not affect the isotopic variability measured by the Iso-FD approach.

During a field trial, data from the Iso-FD tracked well with data from both the two-point and multi-point subsurface Keeling plots. In most cases, departures from the relatively stable Iso-FD signatures (for example around day 265) are well correlated with sudden spikes in $CO_2$ flux, as measured by a LiCOR LI-8100 located near the Iso-FD chamber (data not shown). It is also important to consider here, that the subsurface methods are measuring a more stable, time-integrated (because of diffusive processes) signal and therefore deviations seen in the Iso-FD data may in face be high frequency changes in microbial/root processes near the surface which do no last for a sufficient period of time to express themselves in the soil gas concentrations. These field data are not shifted to take into account the offset caused by drawing air from the chamber, largely because of the uncertainty associated with the offset calculated during the Flux Generator testing. Assuming, however, the offset is similar to the estimated 1.958‰ the isotopic signature measured by the probes would fall between the root respired isotopic composition from the site (−27‰±1.6‰, unpublished incubation data) and the fluxes measured using the subsurface Keeling plot which will tend to be biased toward deeper soil respiration rather than the very near surface where the bulk of the fine root mass is at this site (~60% of fine root mass within the first 15 cm of soil is in the top 0-5 cm depth increment).

The invention claimed is:

1. A method for determining flux of a component of a gas of interest, the method comprising:
    placing a first chamber having an open bottom sealably in contact with a soil location, the first chamber being in communication with the soil via an inlet membrane covering the open bottom and being in communication with atmosphere surrounding the first chamber via one or more outlet membranes;
    after allowing gas in the first chamber to reach equilibrium, measuring with a measuring device a first concentration of a first isotopologue of the gas of interest within the first chamber and a first concentration of a second isotopologue of the gas of interest within the first chamber; and
    measuring with a measuring device an atmospheric concentration of the first isotopologue of the gas of interest and an atmospheric concentration of the second isotopologue of the gas of interest.

2. The method of claim 1, further comprising placing a second chamber having a closed bottom in a vicinity of the first chamber, the second chamber being in communication with the surrounding atmosphere via one or more outlet membranes of the second chamber, wherein measuring the atmospheric concentration of the first isotopologue comprises measuring the concentration of the first isotopologue within the second chamber after allowing gas in the second chamber to reach equilibrium and measuring the atmospheric concentration of the second isotopologue comprises measuring the concentration of the second isotopologue within the second chamber after allowing gas in the second chamber to reach equilibrium.

3. The method of claim 2, further comprising:
    connecting an outlet port of the first chamber via a valving system to an input port of a measuring device;
    connecting an outlet port of the second chamber via the valving system to the input port of the measuring device.

4. The method of claim 3 further comprising:
    prior to measuring the first concentrations of the first isotopologue and the second isotopologue within the first chamber, controlling the valving system to allow communication between the outlet port of the first chamber and the input port of the measuring device; and
    prior to measuring the atmospheric concentrations of the first isotopologue the second isotopologue within the second chamber, controlling the valving system to allow communication between the outlet port of the second chamber and the input port of the measuring device.

5. The method of claim 4, wherein the valving system is controlled such that the first concentrations of the first isotopologue and the second isotopologue and the atmospheric concentrations of the first isotopologue and the second isotopologue are measured at substantially the same time.

6. The method of claim 1, wherein first concentration of the first isotopologue within the first chamber and first concentration of the second isotopologue within the first chamber are measured at substantially the same time, and wherein the atmospheric concentration of the first isotopologue and the atmospheric concentration of the second isotopologue are measured at substantially the same time.

7. The method of claim 1 further comprising:
using a processor, determining a flux of the first isotopologue through the inlet membrane of the first chamber relative to a flux of the second isotopologue through the inlet membrane of the first chamber based on the measured first concentration of the first isotopologue, the measured first concentration of the second isotopologue, the measured atmospheric concentration of the first isotopologue, the measured atmospheric concentration of the second isotopologue, the diffusivity of the first isotopologue through the one or more outlet membranes and the diffusivity of the second isotopologue through the one or more outlet membranes.

8. The method of claim 7, wherein the flux of the first isotopologue through the inlet membrane of the first chamber relative to a flux of the second isotopologue through the inlet membrane of the second chamber is determined according to:

$$F_{rel} = \frac{D^{g1}\left(C_{FD}^{g1} - C_{atm}^{g1}\right)}{D^{g2}\left(C_{FD}^{g2} - C_{atm}^{g2}\right)}$$

wherein $F_{rel}$ is the flux of the first isotopologue through the inlet membrane of the first chamber relative to a flux of the second isotopologue through the inlet membrane of the second chamber, $D^{g1}$ is the diffusivity of the first isotopologue through the one or more outlet membranes, $D^{g2}$ is the diffusivity of the second isotopologue through the one or more outlet membranes, $C_{FD}^{g1}$ the measured first concentration of the first isotopologue, $C_{atm}^{g2}$ is the measured atmospheric concentration of the first isotopologue, $C_{FD}^{g2}$ is the measured first concentration of the second isotopologue, and $C_{atm}^{g2}$ is the measured atmospheric concentration of the second isotopologue.

9. The method of claim 1, wherein the first chamber reaches equilibrium via diffusion of soil gases into the first chamber through the inlet member covering the bottom opening and diffusion of gases through the one or more outlet membranes between the first chamber and atmosphere surrounding the first chamber.

10. The method of claim 1, wherein the first concentration of the first isotopologue, the first concentration of the second isotopologue, the atmospheric concentration of the first isotopologue and the atmospheric concentration of the second isotopologue are measured by one or more spectrometers.

11. The method of claim 10, wherein one or more spectrometers are cavity ring down spectrometers.

12. The method of claim 1, wherein measuring the first concentration of the first isotopologue within the first chamber and the concentration of a second isotopologue within the first chamber comprises extracting gas in the first chamber for a time period in which constant concentrations of the first isotopologue and second isotopologue in the first chamber are maintained.

13. The method of claim 1, wherein measuring the first concentration of the first isotopologue within the first chamber and the first concentration of a second isotopologue within the first chamber comprises:
extracting of gas from the first chamber;
measuring the first concentration of the first isotopologue in the extracted gas and the first concentration of the second isotopologue in the extracted gas; and
inserting extracted gas back into the first chamber.

14. The method of claim 1, wherein measuring the first concentration of the first isotopologue within the first chamber and the first concentration of a second isotopologue within the first chamber comprises:
extracting into a sampling container a volume of gas from the first chamber; and
measuring the first concentration of the first isotopologue of the gas of interest and the first concentration of the second isotopologue of the gas of interest in the volume of gas extracted.

15. The method of claim 13, wherein the volume of gas extracted is measured off-site.

16. The method of claim 1, further comprising:
after measuring the first concentration of the first isotopologue within the first chamber and the first concentration of the second isotopologue within the first chamber, opening a lid of the first chamber to expose a cavity of the first chamber to the surrounding atmosphere;
closing the lid of the first chamber to allow gas in the first chamber to reach equilibrium; and
after allowing gas in the first chamber to reach equilibrium, measuring an additional concentration of the first isotopologue within the first chamber and an additional concentration of the second isotopologue within the first chamber.

17. A system for determining flux of a component of a gas of interest comprising:
first chamber comprising chamber walls and a lid defining a first cavity having a first size and shape, the chamber walls also defining an opening for sealably contacting the cavity with a soil location, the first chamber walls further defining one or more first outlet openings providing communication between the cavity and atmosphere surrounding the first chamber; the first chamber further comprising an inlet membrane covering the opening having an inlet membrane diffusivity and one or more first outlet membranes covering the one or more first outlet openings having a lower diffusivity than the inlet membrane diffusivity; and
one or more measuring devices for measuring a first concentration of a first isotopologue of the gas of interest within the first cavity, a first concentration of a second isotopologue of the gas of interest within the cavity, an atmospheric concentration of the first isotopologue of the gas of interest and an atmospheric concentration of the second isotopologue of the gas of interest.

18. The system of claim 17, further comprising:
a second chamber comprising chamber walls and a lid defining a second cavity having a height and width substantially equal to the shape and size of the first cavity, the chamber walls further defining one or more second outlet openings being shaped and sized substantially equal to the one or more first outlet openings, the one or more second outlet openings providing communication between the second cavity and atmosphere surrounding the second chamber, the second chamber further comprising one or more second outlet membranes covering the one or more second outlet openings having a diffusivity substantially equal to the diffusivity of the one or more first outlet membranes;

wherein the one or more measuring devices measures the atmospheric concentrations of the first and second isotopologues by measuring concentrations of the first and second isotopologues within the second cavity.

19. The system of claim 17, wherein the first chamber further comprises a lateral wall dividing the cavity into a soil sub-cavity and a reference sub-cavity, the soil sub-cavity sealably contacting the soil location and communicating with the atmosphere surrounding the first chamber through the first outlet openings and the reference sub-cavity being in communication with the surrounding atmosphere via one or more first recesses defined on the inside of the chamber walls, the first recesses contacting bores drilled in the chamber walls, the bores further contacting second recesses defined on the outside of the chamber walls.

20. The system of claim 17 wherein the one or more measuring device is one or more spectrometers.

21. The system of claim 17 wherein the first chamber comprises a first outlet port sealably connecting the first cavity to one or more inputs of the one or more measuring devices.

22. The system of claim 21 wherein the system further comprises a first tube attached to an inlet port of the first chamber, the first cavity being in communication with the surrounding atmosphere through the inlet port and the first tube.

23. The system of claim 21, wherein the first outlet port is connected to the measuring device being further connected to an inlet port of the first chamber to form a continuous flow of gas between the first outlet port and the inlet port via one of the one or more measuring devices, the one of the one or more measuring devices sampling the gas within the continuous flow to measure the first concentration of the first isotopologue and the first concentration of the second isotopologue.

24. The system of claim 17, wherein the lid is selectable between an open and a closed position, wherein in the open position the lid exposes a top opening defined by first chamber walls and the first cavity is in communications with the surrounding atmosphere through the top opening, and wherein in the closed position the lid seals the top opening.

25. The system of claim 17, wherein the first chamber further comprises a sampling port for receiving a sampling container, the sampling port providing communication between the first cavity and the sampling container when received.

26. The system of claim 17 further comprising a controller configured for :
after allowing gas in the first cavity to reach equilibrium, controlling one of the one or more the measuring device to measure the first concentration of the first isotopologue within the first cavity and the first concentration of the second isotopologue within the first cavity.

27. The system of claim 26, wherein the controller is configured to periodically control one of the one or more measuring devices to measure of the first concentration of the first isotopologue within the first cavity and the first concentration of the second isotopologue within the first cavity.

28. The system of claim 26, wherein the controller is further configured for:
determining a flux of the first isotopologue through the inlet membrane of the first chamber relative to a flux of the second isotopologue through the inlet membrane of the first chamber based on the measured first concentration of the first isotopologue, the measured first concentration of the second isotopologue, the measured atmospheric concentration of the first isotopologue, the measured atmospheric concentration of the second isotopologue, diffusivity of the first isotopologue through the one or more outlet membranes and diffusivity of the second isotopologue through the one or more outlet membranes.

29. The system of claim 28, wherein the flux of the first isotopologue through the inlet membrane of the first chamber relative to a flux of the second isotopologue of the gas of interest through the inlet membrane of the second chamber is determined according to:

$$F_{rel} = \frac{D^{g1}(C_{FD}^{g1} - C_{atm}^{g1})}{D^{g2}(C_{FD}^{g2} - C_{atm}^{g2})}$$

wherein $F_{rel}$ is the flux of the first isotopologue through the inlet membrane of the first chamber relative to a flux of the second isotopologue through the inlet membrane of the second chamber, $D^{g1}$ is the diffusivity of the first isotopologue through the one or more outlet membranes, $D^{g2}$ is the diffusivity of the second isotopologue through the one or more outlet membranes, $C_{FD}^{g1}$ is the measured first concentration of the first isotopologue, $C_{atm}^{g2}$ is the measured atmospheric concentration of the first isotopologue, $C_{g2}^{FD}$ is the measured first concentration of the second isotopologue, and $C_{atm}^{g2}$ is the measured atmospheric concentration of the second isotopologue.

30. The system of claim 17, wherein the one or more measuring devices is one or more spectrometers.

31. The system of claim 17, wherein the first chamber comprises a first outlet port sealably connecting the first cavity to an input of one of the one or more measuring devices via a valving system and the second chamber comprises a second outlet port sealably connecting the second cavity to the input of said one of the one or more measuring devices via the valving system, the system further comprising a controller being further configured for:
controlling the valving system to selectively allow communication between the first cavity or second cavity with the input of said one of the one or more measuring devices.

32. The method of claim 31, wherein the controller controls valving system and said one of the one or more measuring devices such that the first concentrations of the first isotopologue and the second isotopologue and the atmospheric concentrations of the first isotopologue and the second isotopologue are measured at substantially the same time.

* * * * *

UNITED STATES PATENT AND TRADEMARK OFFICE
CERTIFICATE OF CORRECTION

PATENT NO. : 8,681,336 B2  Page 1 of 1
APPLICATION NO. : 13/417625
DATED : March 25, 2014
INVENTOR(S) : Nicholas R. Nickerson et al.

It is certified that error appears in the above-identified patent and that said Letters Patent is hereby corrected as shown below:

Specification

Column 19, line 40, delete "$C_{FD}{}^{g1}$" and replace with --$C_{FD}^{g1}$--.

Column 19, line 41, delete "$C_{atm}{}^{g2}$" and replace with --$C_{atm}^{g1}$--.

Column 19, line 42, delete "$C_{FD}{}^{g2}$" and replace with --$C_{FD}^{g2}$--.

Column 19, line 43, delete "$C_{atm}{}^{g2}$" and replace with --$C_{atm}^{g2}$--.

Column 22, line 31, delete "$C_{FD}{}^{g1}$" and replace with --$C_{FD}^{g1}$--.

Column 22, line 32, delete "$C_{atm}{}^{g2}$" and replace with --$C_{atm}^{g1}$--.

Column 22, line 33, delete "$C_{g2}{}^{FD}$" and replace with --$C_{FD}^{g2}$--.

Column 22, line 34, delete "$C_{atm}{}^{g2}$" and replace with --$C_{atm}^{g2}$--.

Signed and Sealed this
Thirteenth Day of October, 2015

Michelle K. Lee
*Director of the United States Patent and Trademark Office*